United States Patent [19]

François et al.

[11] Patent Number: 5,700,814
[45] Date of Patent: Dec. 23, 1997

[54] SABELUZOLE ORAL SUSPENSIONS

[75] Inventors: Marc Karel Jozef François, Kalmthout; Christine Frieda Augusta Agemans, Oelegem, both of Belgium

[73] Assignee: Janssen Pharmaceutica, N.V., Beerso, Belgium

[21] Appl. No.: 809,827

[22] PCT Filed: Oct. 6, 1995

[86] PCT No.: PCT/EP95/03966

§ 371 Date: Mar. 27, 1997

§ 102(e) Date: Mar. 27, 1997

[87] PCT Pub. No.: WO96/11687

PCT Pub. Date: Apr. 25, 1996

[30] Foreign Application Priority Data

Oct. 14, 1994 [EP] European Pat. Off. ............ 94202986

[51] Int. Cl.$^6$ ............................................. A61K 31/445
[52] U.S. Cl. ........................................................ 514/321
[58] Field of Search .......................................... 514/321

[56] References Cited

U.S. PATENT DOCUMENTS

| | | | |
|---|---|---|---|
| 4,861,785 | 8/1989 | Stokbroekx et al. | 514/321 |
| 5,434,168 | 7/1995 | Stokbroekx et al. | 514/321 |

*Primary Examiner*—Raymond Henley, III
*Attorney, Agent, or Firm*—Charles J. Metz

[57] ABSTRACT

An aqueous suspension for oral administration comprising sabeluzole and a pharmaceutically acceptable carrier, having a pH in the range from 8 to 10; processes for preparing the same.

22 Claims, No Drawings

SABELUZOLE ORAL SUSPENSIONS

Cross-Reference to Related Applications

This application is the national stage of application No. PCT/EP 95/03966, filed on Oct. 6, 1995, which application claims priority from EP 94.202.986.9, filed on Oct. 14, 1994.

The invention relates to physicochemically stable sabeluzole formulations having a satisfactory taste and aftertaste.

In U.S. Pat No. 4,861,785 then are described compounds having antihypoxic and antianoxic properties useful in indications such as shock, cardiac arrest and severe blood loss. Among these compounds features 4-(2-benzothiazolylmethylamino-α-[(4-fluorophenoxy)methyl]-1-piperidineethanol, which is generically known as sabeluzole. Subsequent investigations have shown the potential of sabeluzole in the treatment of patents suffering from chronic neuro-degenerative diseases such as dementia of the Alzheimer type (DAT) or Alzheimer's disease, amyotrophic lateral sclerosis (ALS), dementia associated with Parkinson's disease and other central nervous system diseases which are characterized by progressive dementia.

Administration of an oral dosage form is the preferred route of administration for many pharmaceuticals because it provides for easy, low-cost administration. However, patient compliance can be a problem when the patient is requested to swallow a solid formulation such as a tablet or a capsule. Therefore, the development of a liquid oral formulation is often desirable.

The development of a liquid oral formulation of sabeluzole is hampered by the unpleasant bitter taste of the compound. The bitter flavour of sabeluzole is inevitably tasted during drinking or immediately after swallowing a solution comprising the compound. A clear improvement in taste is observed using a suspension of sabeluzole instead of a solution of the compound. In particular the bitter aftertaste is significantly reduced. The development of a useful suspension of sabeluzole, however, is hampered by chemical stability problems of the compound. In particular, aqueous suspensions of sabeluzole at pH 7 suffer from degradation of sabeluzole and have an unacceptable shelf-life. A stable sabeluzole suspension was prepared by maintaining the pH in a strict range from about 8 to 10. These suspensions were further specifically adapted so as to allow them to be diluted with cold beverages such as fruit juice and also hot beverages such as tea, cocoa and coffee. These features are considered essential properties in a medicament which has to be administered to patients whose compliance with therapy is a major concern.

The present invention is concerned with stable aqueous sabeluzole suspensions having a pH in the range from 8 to 10. In particular, the invention relates to aqueous suspensions for oral administration comprising sabeluzole and a pharmaceutically acceptable carrier, having a pH in the range from 8 to 10.

The term "stable" as used herein relates to compositions wherein the decrease in the sabeluzole content is less than 10%, preferably less than 5% and most preferably less than 2%, after storage at room temperature for up to 3 months.

The term sabeluzole as used hereinabove also comprises the solvates which sabeluzole is able to form and said solvates are meant to be included within the scope of the present invention. Examples of such solvates are, e.g. the hydrates, alcoholates and the like.

Sabeluzole has an asymmetric carbon atom and the absolute configuration of this asymmetric centre may be indicated by the stereochemical descriptors R and S. Unless otherwise mentioned or indicated, the chemical designation of compounds denotes the mixture of all possible stereochemically isomeric forms, in particular the racemate.

Two polymorphs of sabeluzole base are known. The higher melting polymorph I (mp. 101.7° C., maximum 105.3° C., heat of fusion=99.6 J/g) can be distinguished easily by its DSC characteristics from the lower melting polymorph II (mp. 88.9° C., maximum 91.6° C., heat of fusion 84.2 J/g). X-ray diffraction analysis has confirmed the existence of the two polymorphs. Polymorph II is metastable and dissolves considerably more rapidly than polymorph I, especially at mildly acidic pH values. Polymorph II when substantially crystallographically pure is stable for all practical purposes. Preferably, the suspensions include the stable polymorph I.

Hereinafter, the amounts of each of the ingredients in the compositions are expressed as percentages by weight based on the total volume of the formulation, unless otherwise indicated.

In particular, the concentration of sabeluzole in the present suspensions may range from 0.01% to 5%, preferably from 0.05% to 1%, more preferably from 0.1% to 0.5% and in particular is about 0.1%.

Chemical degradation of sabeluzole in suspension is prevented by raising the pH to slightly to moderately basic, that is to pH 8 to 10, in particular to pH of approximately 9. A maximum trade-off between two mutually contrary prerequisites, namely increasing chemical stability with increasing pH and decreasing organoleptic properties with increasing pH, is reached at about pH 9. In view of the further prerequisite that the suspension should be dilutable with a variety of beverages, said pH ranges are created by using a buffer system. Buffer systems comprise mixtures of appropriate amounts of an acid such as phosphoric, hydrochloric or boric acid, and a base, in particular sodium carbonate, sodium bicarbonate, sodium hydroxide or disodium hydrogen phosphate. Said buffer systems should maintain the pH of the formulation in the range from 8 to 10, more preferably in the range from 8.5 to 9.5 and most preferably at about 9. Preferably, a carbonate buffer comprising sodium carbonate, sodium bicarbonate and/or sodium hydroxide or hydrochloric acid is used.

The oral suspension may further comprise various pharmaceutically acceptable ingredients such as suspending agents, wetting agents, stabilizing agents, preservatives, and the like. Suitable suspending agents are cellulose derivatives, e.g. dispersible cellulose (=a mixture of microcrystalline cellulose and carboxymethylcellulose sodium), hypromellose (=hydroxypropyl methylcellulose), and the like. Preferably, dispersible cellulose (Avicel RC591®) is used in an amount of 0.1 to 2%, more preferably in an amount of about 1.2%. The addition of Avicel RC591® results in thixotropic properties of the suspension, i.e. the suspension becomes temporarily liquid when shaken or stirred and returns to a gel on standing. The gel structure of the suspension upon standing precludes the suspended particles to precipitate. Hydrocolloids such as hypromellose stabilize the suspension by adsorption to the suspended particles. Hypromellose (hydroxypropyl methylcellulose) has proven to be particularly useful except when the suspension is to be diluted with a hot beverage because the agent tends to gel and flocculate. Fortunately, it has been found that the incorporation of hypromellose is entirely optional and that aqueous sabeluzole suspensions without hypromellose meet all the prerequisites set out hereinbefore and, in addition, can easily be diluted with hot beverages without the problem of flocculation of any of the adjuvants used in the formula. If used at all, an amount of 0.1% to 2.5% in particular about 0.25% (w/v), of hypromellose, is adequate.

Suitable wetting agents are, for example, polyoxyethylene derivatives of sorbitan esters, e.g. polysorbate 20 (Tween 20®), polysorbate 40 (=Tween 40®), polysorbate 60 (=Tween 60®), and the like. In particular, polysorbate 20 is used in an amount of 0.01 to 1%, preferably in an amount of approximately 0.025%.

Suitable preservatives which are stable at the alkaline conditions of the suspension are, e.g. propylene glycol, ethanol and the like. Preferably, propylene glycol is used in an amount of 5 to 30% (v/v), more preferably in an amount of about 20% (v/v).

In order to improve the palatability of the suspension sweeteners and/or flavouring substances may be added. Sweeteners have been found to improve the organoleptic properties of aqueous sabeluzole suspensions at pH 8 to 10 very markedly. Flavouring agents on the other hand appear to be entirely optional; while definitely influencing the taste of the suspension, they do not appear to improve the organoleptic properties of said suspensions. Suitable sweeteners comprise saccharin, sodium or calcium saccharin, aspartame, acesulfame potassium, sodium cyclamate, alitame, a dihydrochalcone sweetener, monellin, stevioside or sucralose (4,1',6'-trichloro-4,1',6-trideoxy-galactosucrose), or a bulk sweetener such as sorbitol, mannitol, fructose, sucrose, maltose, isomalt, glucose, hydrogenated glucose syrup, xylitol, caramel or honey. In particular, polyalcohols are used as sweetening agents. The latter show the additional advantage that they increase the viscosity of the suspension and enhance the antimicrobial efficacy of, e.g. propylene glycol. Preferably, sorbitol (in a 70% w/v solution) is used in an amount of 5 to 30% (v/v), more preferably in an amount of about 20% (v/v).

Suitable flavours which may optionally be added are Chocolate flavour, Herb flavour, Caramel Chocolate flavour, Mint Cool flavour, Fantasy flavour and fruit flavours such as cherry, raspberry, black currant or strawberry flavour, and the like. Each flavour may be present in the final composition in a concentration ranging up to 1%. Combinations of flavours may advantageously be used. Obviously, the flavours used preferably do not undergo any change or loss of taste and colour under the alkaline conditions of the formulation.

The subject suspensions may be presented in art-known containers such as bottles, spray devices, sachets, and the like. Optionally, the suspensions are manufactured in unit-dose containers, e.g. unit-dose sachets or unit-dose bottles.

In general it is contemplated that an effective daily amount would be from 1 to 40 mg, preferably from 10 to 20 mg of active ingredient. It is evident that said effective daily amount may be lowered or increased depending on the response of the treated subject and/or depending on the evaluation of the physician prescribing the compounds of the instant invention. The effective daily amount ranges mentioned hereinabove are therefore guidelines only and are not intended to limit the scope or use of the invention to any extent.

In particular, the present invention relates to suspensions comprising:

(a) 0.01 to 5% (w/v) sabeluzole;
(b) 0.2 to 4% (w/v) suspending agents;
(c) up to 30% (w/v) sweeteners;
(d) up to 30% (v/v) preservatives;
(e) 0.01 to 1% (w/v) wetting agent;
(f) buffer substances to fix the pH in the range from 8 to 10; and
(g) water q.s. ad 100%.

More particularly, the present invention is concerned with suspensions comprising:

(a) 0.05 to 1% (w/v) sabeluzole;
(b) 0.8 to 1.5% (w/v) dispersible cellulose and optionally 0.1 to 0.5% (w/v) hypromellose;
(c) 10 to 30% (v/v) sorbitol solution (70% (w/v) in water);
(d) 10 to 30% (v/v) propylene glycol;
(e) 0.01 to 1% (w/v) polysorbate 20;
(f) buffer substances to fix the pH in the range from 8.5 to 9.5; and
(g) water q.s. ad 100%.

Preferably, the invention relates to a suspension comprising approximately:

(a) 0.1% (w/v) sabeluzole polymorph I;
(b) 1.2% (w/v) dispersible cellulose and optionally 0.25% (w/v) hypromellose;
(c) 20% (v/v) sorbitol 70% (w/w) solution;
(d) 20% (v/v) propylene glycol;
(e) 0.025% (w/v) polysorbate 20;
(f) sodium carbonate and hydrochloric acid to fix the pH at about 9;
(g) water q.s. ad 100%

In a particular aspect of the invention the above suspensions may include one or more flavouring substances.

Further, the present invention relates to the preparation of the described suspensions. The preparation involves the intimate mixing of the active ingredient with the carrier ingredients. In particular, the preparation involves the following steps: (a) the suspending agents, wetting agents, sweeteners and preservatives are mixed with an amount of water;, (b) sabeluzole is mixed with phase (a); and (c) the pH is fixed in the range from 8 to 10.

Optionally, the above procedure is conducted under an inert atmosphere, e.g. nitrogen or oxygen-free argon. It is advantageous to use a micronized form of sabeluzole, in particular material having an average particle size of less than 100 microns, preferably less than 75 microns, and in particular having a mean particle size of not more than 15 microns. Micronized forms can be prepared by micronization techniques known in the art, e.g. by milling in appropriate mills and sieving through appropriate sieves.

The following examples are intended to illustrate the scope of the present invention in all its aspects.

EXAMPLE 1

| F1 Ingredient | Quantity |
| --- | --- |
| Sabeluzole polymorph I | 2.5 mg |
| Polysorbate 20 | 0.25 mg |
| Dispersible cellulose | 12 mg |
| Propylene glycol | 200 µl |
| Hypromellose 2910 | 2.5 mg |
| Sorbitol 70% (w/w) solution | 200 µl |
| Sodium carbonate | 5 mg |
| Concentrated hydrochloric acid | q.s. ad pH = 9 |
| Purified water | q.s. ad 1 ml |

Preparation (1) 2.5 mg hypromellose 2910 was added upon stirring to an amount of purified water at 90°–95° C.;

(2) phase (1) was cooled to ambient temperature;

(3) 200 μl sorbitol 70% (w/w) solution, 0.25 mg polysorbate 20, 200 μl propylene glycol and 12 mg dispersible cellulose were homogeneously dispersed in an amount of purified water;

(4) phases (2) and (3) were mixed;

(5) 2.5 mg sabeluzole polymorph I was added to phase (4);

(6) 5 mg sodium carbonate was dissolved in an amount of purified water;

(7) phases (5) and (6) were mixed upon stirring;

(8) the pH of phase (7) was adjusted to about 9 with concentrated hydrochloric acid; and (9) phase (8) was diluted to the desired end volume.

In a similar way there were prepared:

| F2 Ingredient | Quantity |
| --- | --- |
| Sabeluzole polymorph I microfine | 5 mg |
| Polysorbate 20 | 0.25 mg |
| Dispersible cellulose | 12 mg |
| Propylene glycol | 200 μl |
| Hypromellose 2910 | 2.5 mg |
| Sorbitol 70% (w/w) solution | 150 μl |
| Sodium carbonate | 2.5 mg |
| Herb flavour | 0.53 mg |
| Concentrated hydrochloric acid | q.s. ad pH = 9 |
| Sodium hydroxide | q.s. ad pH = 9 |
| Purified water | q.s. ad 1 ml |

| F3: Ingredient | Quantity |
| --- | --- |
| Sabeluzole polymorph I microfine | 5 mg |
| Polysorbate 20 | 0.25 mg |
| Dispersible cellulose | 12 mg |
| Propylene glycol | 200 μl |
| Hypromellose 2910 | 2.5 mg |
| Sorbitol 70% (w/w) solution | 150 μl |
| Sodium carbonate | 5 mg |
| Herb flavour | 0.53 mg |
| Concentrated hydrochloric acid | q.s. ad pH = 9 |
| Sodium hydroxide | q.s. ad pH = 9 |
| Purified water | q.s. ad 1 ml |

| F4: Ingredient | Quantity |
| --- | --- |
| Sabeluzole polymorph I microfine | 5 mg |
| Polysorbate 20 | 0.25 mg |
| Dispersible cellulose | 12 mg |
| Propylene glycol | 200 μl |
| Hypromellose 2910 | 2.5 mg |
| Sorbitol 70% (w/w) solution | 150 μl |
| Sodium carbonate | 3.18 mg |
| Sodium bicarbonate | 5.88 mg |
| Herb flavour | 0.53 mg |
| Concentrated hydrochloric acid | q.s. ad pH = 9.5 |
| Sodium hydroxide | q.s. ad pH = 9.5 |
| Purified water | q.s. ad 1 ml |

| F5: Ingredient | Quantity |
| --- | --- |
| Sabeluzole polymorph I | 1 mg |
| Polysorbate 20 | 0.25 mg |
| Dispersible cellulose | 12 mg |
| Propylene glycol | 200 μl |
| Hypromellose 2910 | 2.5 mg |
| Sorbitol 70% (w/w) solution | 200 μl |
| Sodium carbonate | 5 mg |
| Concentrated hydrochloric acid | q.s. ad pH = 9 |
| Purified water | q.s. ad 1 ml |

| F6: Ingredient | Quantity |
| --- | --- |
| Sabeluzole polymorph I | 2.5 mg |
| Polysorbate 20 | 0.25 mg |
| Dispersible cellulose | 12 mg |
| Propylene glycol | 200 μl |
| Sorbitol 70% (w/w) solution | 200 μl |
| Sodium carbonate | 5 mg |
| Concentrated hydrochloric acid | q.s. ad pH = 9 |
| Purified water | q.s. ad 1 ml |

| F7: Ingredient | Quantity |
| --- | --- |
| Sabeluzole polymorph I microfine | 5 mg |
| Polysorbate 20 | 0.25 mg |
| Dispersible cellulose | 12 mg |
| Propylene glycol | 200 μl |
| Sorbitol 70% (w/w) solution | 150 μl |
| Sodium carbonate | 2.5 mg |
| Herb flavour | 0.53 mg |
| Concentrated hydrochloric acid | q.s. ad pH = 9 |
| Sodium hydroxide | q.s. ad pH = 9 |
| Purified water | q.s. ad 1 ml |

| F8: Ingredient | Quantity |
| --- | --- |
| Sabeluzole polymorph I microfine | 5 mg |
| Polysorbate 20 | 0.25 mg |
| Dispersible cellulose | 12 mg |
| Propylene glycol | 200 μl |
| Sorbitol 70% (w/w) solution | 150 μl |
| Sodium carbonate | 5 mg |
| Herb flavour | 0.53 mg |
| Concentrated hydrochloric acid | q.s. ad pH = 9 |
| Sodium hydroxide | q.s. ad pH = 9 |
| Purified water | q.s. ad 1 ml |

| F9: Ingredient | Quantity |
| --- | --- |
| Sabeluzole polymorph I microfine | 5 mg |
| Polysorbate 20 | 0.25 mg |
| Dispersible cellulose | 12 mg |
| Propylene glycol | 200 μl |
| Sorbitol 70% (w/w) solution | 150 μl |
| Sodium carbonate | 3.18 mg |
| Sodium bicarbonate | 5.88 mg |
| Herb flavour | 0.53 mg |
| Concentrated hydrochloric acid | q.s. ad pH = 9.5 |

-continued

P9:
| Ingredient | Quantity |
| --- | --- |
| Sodium hydroxide | q.s. ad pH = 9.5 |
| Purified water | q.s. ad 1 ml |

P10:
| Ingredient | Quantity |
| --- | --- |
| Sabeluzole polymorph I | 1 mg |
| Polysorbate 20 | 0.25 mg |
| Dispersible cellulose | 12 mg |
| Propylene glycol | 200 μl |
| Sorbitol 70% (w/w) solution | 200 μl |
| Sodium carbonate | 5 mg |
| Concentrated hydrochloric acid | q.s. ad pH = 9 |
| Purified water | q.s. ad 1 ml |

EXAMPLE 2

The suspensions as described hereinabove were stored for 3.5 months at room temperature. The concentration of sabeluzole had not significantly changed after storage. No degradation products were detected. Hence, the described suspensions are in compliance with the requirements of a stable formulation as set forth hereinabove.

We claim:

1. An aqueous suspension for oral administration comprising sabeluzole and a pharmaceutically acceptable carrier, having a pH in the range from 8 to 10.

2. A suspension according to claim 1 wherein the active ingredient is sabeluzole polymorph I.

3. A suspension according to claim 1 wherein the pH range from 8 to 10 is created with a carbonate buffer comprising sodium carbonate, sodium bicarbonate and/or sodium hydroxide or hydrochloric acid.

4. A suspension according to claim 3 wherein the pH is approximately 9.

5. A suspension according to claim 1 further comprising a suspending agent.

6. A suspension according to claim 5 wherein the suspending agent is Avicel RC591® in an amount of 0.1 to 2% (w/v).

7. A suspension according to claim 1 further comprising a sweetener.

8. A suspension according to claim 7 wherein the sweetener is a sorbitol solution (70% (v/v)) in an amount of 5 to 30% (w/v).

9. A suspension according to claim 1 comprising (a) 0.01 to 5% (w/v) sabeluzole polymorph I;

(b) 0.2 to 4% (w/v) suspending agents;

(c) up to 30% (w/v) sweeteners;

(d) up to 30% (v/v) preservatives;

(e) 0.01 to 1% (w/v) wetting agent;

(f) buffer substances to fix the pH in the range from 8 to 10; and (g) water q.s. ad 100%.

10. A suspension according to claim 9 comprising:

(a) 0.05 to 1% (w/v) sabeluzole polymorph I;

(b) 0.8 to 1.5% (w/v) dispersible cellulose and optionally 0.1 to 0.5% (w/v) hypromellose;

(c) 10 to 30% (v/v) sorbitol solution;

(d) 10 to 30% (v/v) propylene glycol;

(e) 0.01 to 1% (w/v) polysorbate 20;

(f) buffer substances to fix the pH in the range from 8.5 to 9.5; and (g) water q.s. ad 100%.

11. A suspension according to claim 10 comprising (a) 0.1% (w/v) sabeluzole polymorph I;

(b) 1.2% (w/v) dispersible cellulose and optionally 0.25% (w/v) hypromellose;

(c) 20% (v/v) sorbitol 70% (w/w) solution;

(d) 20% (v/v) propylene glycol;

(e) 0.025% (w/v) polysorbate 20;

(f) sodium carbonate and hydrochloric acid to fix the pH at about 9;

(g) water q.s. ad 100%.

12. A method of treating hypoxic or anoxic conditions in patients which comprises administering to such patients an effective amount of the suspension of claim 1.

13. A method of treating hypoxic or anoxic conditions in patients which comprises administering to such patients an effective amount of the suspension of claim 2.

14. A method of treating hypoxic or anoxic conditions in patients which comprises administering to such patients an effective amount of the suspension of claim 3.

15. A method of treating hypoxic or anoxic conditions in patients which comprises administering to such patients an effective amount of the suspension of claim 4.

16. A method of treating hypoxic or anoxic conditions in patients which comprises administering to such patients an effective amount of the suspension of claim 5.

17. A method of treating hypoxic or anoxic conditions in patients which comprises administering to such patients an effective amount of the suspension of claim 6.

18. A method of treating hypoxic or anoxic conditions in patients which comprises administering to such patients an effective amount of the suspension of claim 7.

19. A method of treating hypoxic or anoxic conditions in patients which comprises administering to such patients an effective amount of the suspension of claim 8.

20. A method of treating hypoxic or anoxic conditions in patients which comprises administering to such patients an effective amount of the suspension of claim 9.

21. A method of treating hypoxic or anoxic conditions in patients which comprises administering to such patients an effective amount of the suspension of claim 10.

22. A method of treating hypoxic or anoxic conditions in patients which comprises administering to such patients an effective amount of the suspension of claim 11.

* * * * *